(12) United States Patent
Costantini et al.

(10) Patent No.: US 6,559,339 B1
(45) Date of Patent: May 6, 2003

(54) METHOD FOR CRYSTALLIZING CARBOXYLIC ACID

(75) Inventors: Michel Costantini, Lyons (FR); Eric Fache, Caluire et Cuire (FR)

(73) Assignee: Rhodia Fiber & Resin Intermediates, Courbevoie Cedex (FR)

( * ) Notice: Subject to any disclaimer, the term of this patent is extended or adjusted under 35 U.S.C. 154(b) by 0 days.

(21) Appl. No.: 09/787,127

(22) PCT Filed: Sep. 14, 1999

(86) PCT No.: PCT/FR99/02181

§ 371 (c)(1),
(2), (4) Date: May 31, 2001

(87) PCT Pub. No.: WO00/15597

PCT Pub. Date: Mar. 23, 2000

(30) Foreign Application Priority Data

Sep. 14, 1998 (FR) .............................................. 98 11590
Jun. 29, 1999 (FR) .............................................. 99 08590

(51) Int. Cl.[7] .............................................. C07C 51/42
(52) U.S. Cl. ..................................................... 562/593
(58) Field of Search ................................ 562/593, 590

(56) References Cited

U.S. PATENT DOCUMENTS

| | | | |
|---|---|---|---|
| 2,811,548 A | 10/1957 | Ham et al. | |
| 2,949,483 A | 8/1960 | Ham et al. | |
| 5,104,492 A | * 4/1992 | King et al. | ..................... 203/15 |
| 5,463,119 A | * 10/1995 | Kollar | ......................... 562/543 |

FOREIGN PATENT DOCUMENTS

| | | |
|---|---|---|
| CH | 400 116 A | 4/1966 |
| EP | 0 847 980 | 6/1998 |
| JP | 50125973 | 10/1975 |
| SU | 218 150 | 5/1968 |
| WO | 98 35929 | 8/1998 |

OTHER PUBLICATIONS

Database WPI, Section Ch, Derwent Publications Ltd., GB; London, AN 1968–341920, XP002104154 & SU 218 150 A (KV RYASHENTSEV), abstract.

Chemical Abstracts, vol. 84, No. 18, May 3, 1976, Columbus, Ohio, US; Abstract No. 123976q, p. 125; XP002129563, abstract & JP 50 125973 (UBE Industries Ltd.), abstract.

Database Crossfire 'Online' Beilstein Institut fur Literatur der organischen Chemie, XP002129564, Beilstein Registry No. 1209788, see table "Melting point 1–10", reference 3, table "Melting point 41–50", reference 4, table "Melting point 71–80", reference 5 and 6, table "Melting point 81–90", reference 3 & Chem. Ber., vol. 116, No. 4, 1983, pp. 1309–1313, & Yakugaku Zasshi, vol. 81, 1961, p. 1639 & J. Chem. Soc., 1960, p. 1909, 1911 & ZH. Org. Khim., vol. 4, 1968,m pp. 1893–1899, & Chem. Ber., vol. 102, 1969, pp. 3877–3890.

* cited by examiner

Primary Examiner—Richard L. Raymond
Assistant Examiner—Zachary C. Tucker
(74) Attorney, Agent, or Firm—Burns, Doane, Swecker & Mathis, L.L.P.

(57) ABSTRACT

The present invention relates to a process for the crystallization of carboxylic acid, more particularly adipic acid, and a process for manufacturing crystalline carboxylic acid, more specifically a process for treating the reaction medium resulting from the direct oxidation of a hydrocarbon into carboxylic acid such as adipic acid, for example. More specifically, the invention relates to the crystallization of adipic acid from an organic solvent, thus removing the organic impurities contained in the said acid and thus optionally facilitating its purification by a crystallization from water.

20 Claims, No Drawings

METHOD FOR CRYSTALLIZING CARBOXYLIC ACID

This application is a national stage application, filed under 35 U.S.C. 371, of PCT/FR99/0281, filed Sep. 14, 1999.

The present invention relates to a process for the crystallization of carboxylic acid, more particularly adipic acid, and a process for manufacturing crystalline carboxylic acid, more specifically a process for treating the reaction medium from the direct oxidation of a hydrocarbon into carboxylic acid such as adipic acid, for example.

Adipic acid is one of the two starting materials in the preparation of polyamides, such as polyamide 6-6, and of various other polymers. The applications of polyamide 6-6 require highly controlled properties in terms of both chemical and physicochemical composition. In order to obtain such a polymer, it is necessary to have very high purity at the stage of the monomers, such as adipic acid or dicarboxylic acids.

Adipic acid is also one of the important starting materials in the manufacture of polyurethanes.

Depending on the process for the synthesis of adipic acid, the impurities it contains are obviously different. However, it is always necessary to involve a step of purification of the adipic acid produced.

The purification processes generally used are crystallization processes using water as solvent. Such a process is described, for example, in French patent application No. 2,749,299.

However, depending on the synthetic process used and the nature of the product to be purified, the known crystallization solvent, namely water, does not allow certain impurities to be removed, such as organic impurities, for example.

One of the aims of the present invention is to provide a process for the crystallization of carboxylic acid, and more particularly of adipic acid, in solvents capable of removing the said organic impurities.

To this end, the invention provides a process for the crystallization of carboxylic acid, characterized in that the said crystallization or recrystallization is carried out from an organic solvent or a mixture of solvents, at least one of which is an organic solvent, in which the carboxylic acid has a solubility of less than or equal to 15% by weight at a temperature of 20° C., and in that the said solvent is chosen from the families of organic compounds comprising ether, alcohol, ketone, ester, nitrile, amide, sulphoxide or carbonate functions and halogen-containing, nitro or phosphorus-containing organic solvents.

According to a preferred characteristic of the invention, the organic solvent is chosen if the solubility of the carboxylic acid in the said solvent at a temperature of 100° C., or at its boiling point if this is lower than 100° C., is at least 5% higher than that at 20° C. in the same solvent, preferably 10% higher. Furthermore, the solubility at 100° C. should advantageously be at least 15% by weight.

The term "higher solubility" should be understood as meaning a difference in solubility as an absolute value.

The carboxylic acids which can advantageously be crystallized by the process of the invention are preferably dicarboxylic acids such as adipic acid, succinic acid, glutaric acid, terephthalic acid and isophthalic acid. The preferred carboxylic acid of the invention is adipic acid.

As solvents which are suitable for the process of the invention, mention may be made, for example, of 1,4-dioxane; diglyme (diethylene glycol dimethyl ether); aliphatic, cycloaliphatic, aromatic or arylaliphatic ketones such as acetone, methyl isobutyl ketone, methyl ethyl ketone, methyl isopropyl ketone, methyl phenyl ketone, cyclohexanone, tetrahydrofuran; n-butanol; isopropanol; 3-methoxyethanol; acetonitrile; dimethylformamide; acetamide; dichloromethane; ethyl acetate; 1,2-dichloroethane; dimethyl sulphoxide; nitromethane; N-methylpyrrolidone. This list is not exhaustive, the use of other organic solvents which satisfy the general criteria of solubility of the acids being included in the context of the present invention.

The organic solvents can be used alone or as mixtures with another solvent in accordance with the invention or otherwise. Thus, these organic solvents can be used with water.

Advantageously, the organic solvent of the invention has a boiling point which is compatible for carrying out the crystallization under industrially exploitable operating conditions. Thus, suitable solvents advantageously have a boiling point of between 40° C. and 250° C., preferably between 80° C. and 120° C. The crystallization can be performed at atmospheric pressure or under pressure.

The solvents which are suitable for the invention also advantageously have a certain affinity for water, allowing washing of the crystalline adipic acid with water to remove the traces of organic crystallization solvent.

The process of the invention is carried out according to the known techniques of crystallization processes. Briefly, this process comprises a step of dissolution under hot conditions of the carboxylic acid to be crystallized, followed by a step of cooling after optionally filtering the hot acid solution. It is also possible to concentrate the hot acid solution before it is cooled. This crystallization can be improved by any known means and in particular by the use of microwaves.

Needless to say, the crystallization process can be repeated. Similarly, the solution recovered after a crystallization can be concentrated while hot and then cooled in order to recover a further crop of acid.

The present process can be applied to carboxylic acids and more particularly to an adipic acid from various synthetic processes, such as, for example, the adipic acid from the nitric oxidation of cyclohexanol and/or cyclohexanone, from the double hydroxycarbonylation of butadiene or alternatively from the direct oxidation of cyclohexane in air.

The process of the invention applies particularly to the process for the hydroxycarbonylation of butadiene, which consists of a first hydroxycarbonylation of butadiene leading to a mixture of pentenoic acids, mainly 3-pentenoic acid, and a second hydroxycarbonylation performed on the pentenoic acids obtained in the first reaction and leading to adipic acid also containing a certain amount of 2-methylglutaric acid and 2-ethylsuccinic acid, as well as other compounds already originating from the first hydroxycarbonylation reaction, such as γ-valerolactone, unconverted pentenoic acids and methylbutenoic acid. These organic impurities are advantageously removed by a crystallization process in accordance with the invention.

The process of the invention also applies more particularly to the treatment and recovery of carboxylic acid such as adipic acid synthesized by direct oxidation of a hydrocarbon such as cyclohexane with air. This process is described in particular in patent application WO-A-94/07834.

This document describes the oxidation of cyclic hydrocarbons into the corresponding diacids, in a liquid phase comprising a solvent, using a gas containing oxygen and in the presence of an oxidation catalyst such as a cobalt compound, the said solvent comprising an organic acid containing only primary or secondary hydrogen atoms. That patent more particularly develops the phases for treating the final reaction mixture. This treatment consists in separating the diacid formed, by cooling the mixture in order to bring about precipitation of the said diacid, in separating, by filtration, the diacid from two liquid phases, a nonpolar phase which is recycled, and a polar phase which is also at least partially recycled after an optional hydrolysis and a separation of an additional amount of diacid.

That patent more particularly provides a solution for the one-step oxidation of cyclohexane into adipic acid with industrially acceptable selectivity, but it does not provide an industrially applicable solution to the treatment of the reaction mixture obtained from the oxidation, taking into account the separation of the various products and by-products of the reaction, the unconverted materials and in particular the recycling of the catalyst.

Patent EP-A-0,772,581 describes a more complete process for treating the reaction mixture obtained from the direct oxidation of cyclohexane into adipic acid, as well as the recycling of the catalyst. However, in that process, the adipic acid is also crystallized from acetic acid which is a corrosive and expensive solvent, requiring recovery and regeneration operations which greatly affect the general economy of the adipic acid manufacturing process.

To overcome these drawbacks, the Applicant has provided, in its patent EP 084,980, a process for separating adipic acid from acetic acid and then crystallization of this acid from water. However, it has been observed that the crystallization in water of adipic acid does not completely remove the traces of the organic solvent used for the oxidation reaction, in particular when this solvent is a water-miscible carboxylic acid such as acetic acid.

This presence of traces of solvent can complicate the second recrystallization of the adipic acid, in particular as regards the shape of the crystals obtained.

In addition, the Applicant has also found that the presence of oxidation intermediates, such as cyclohexanone, cyclohexanol, cyclohexyl esters, hydroxycarboxylic acids and lactones, is liable to interfere with the separation and purification of the adipic acid. The Applicant has provided, in particular in its French patent application 98/02928, which is not yet published, additional treatment processes for removing the organic impurities.

The crystallization process provided by the present invention removes most of these organic impurities without requiring the use of a corrosive crystallization solvent such as acetic acid or additional treatments. Thus, the acid crystallized according to the process of the invention may be purified more readily by a further crystallization from water, if necessary, to achieve the high purity specifications required in the applications for the manufacture of polyamide or polyurethane.

A subject of the invention is also a process for preparing carboxylic acids by oxidation of a hydrocarbon by direct oxidation and treatment of the reaction medium obtained.

A subject of the invention is, more particularly, a process for treating the reaction mixture obtained from the direct oxidation of hydrocarbons into carboxylic acid, in particular using molecular oxygen or a gas containing it, in the liquid phase, in a solvent and in the presence of a catalyst dissolved in the reaction medium, characterized in that the said process comprises:

when the composition of the reaction mixture allows it, a separation of the phases by settling into two liquid phases: a nonpolar upper phase, essentially containing the unconverted hydrocarbon, and a polar lower phase essentially comprising the solvent, the acids formed, the catalyst and some of the other reaction products and unconverted hydrocarbon;

a distillation of the polar lower phase or, where appropriate, of all of the reaction mixture, thus separating, on the one hand, a distillate comprising at least some of the most volatile compounds such as the unconverted hydrocarbon, the solvent, the reaction intermediates and the water, and, on the other hand, the distillation residue comprising the carboxylic acids formed and the catalyst;

the addition of an organic solvent in accordance with the invention, or a mixture comprising at least one organic solvent in accordance with the invention, to the distillation residue, the separation of the catalyst, which may have precipitated during the addition of the organic solvent, by filtration of the medium, for example, the crystallization of the carboxylic acid from the organic solution of the distillation residue, optionally, a recrystallization of the carboxylic acid recovered from the same solvent or from water.

The separation by settling into two phases of the reaction mixture subjected to the process of the invention depends essentially on the reaction solvent used, the amount of hydrocarbon converted and the water content in the medium.

The hydrocarbons used as starting materials in the process of the invention are, more particularly, alkanes, cycloalkanes and alkylaromatic hydrocarbons containing from 3 to 20 carbon atoms.

Among these hydrocarbons, cycloalkanes, in particular those which have a ring containing from 5 to 12 carbon atoms, are without doubt the most important, since their oxidation leads to dicarboxylic acids.

The most advantageous hydrocarbon is cyclohexane, the oxidation of which leads to adipic acid, one of the base compounds in polyamide 6-6 and one of the diacids most commonly used.

For the purposes of simplicity, the invention will be described very generally with reference to the treatment of the reaction mixtures obtained from the oxidation of cyclohexane into adipic acid, but the process can also be applied to mixtures obtained from the oxidation of other hydrocarbons, and more particularly of other cycloalkanes.

The cyclohexane phase obtained in the optional step of separation by settling is usually reintroduced into a cyclohexane oxidation operation.

The solvent used in the oxidation of the hydrocarbon, preferably cyclohexane, is an at least partial solvent for the carboxylic acid whose preparation is intended. This solvent can be very varied in nature, provided that it is not substantially oxidizable under the reaction conditions. It can be chosen in particular from polar protic solvents and polar aprotic solvents. As polar protic solvents, mention may be made, for example, of carboxylic acids containing only primary or secondary hydrogen atoms, in particular aliphatic acids containing from 1 to 9 carbon atoms, perfluoroalkylcarboxylic acids such as trifluoroacetic acid, water and alcohols. As polar aprotic solvents, mention may be made, for example, of lower alkyl esters (alkyl radical preferably containing from 1 to 4 carbon atoms) of carboxylic acids, in particular of aliphatic carboxylic acids containing from 1 to 9 carbon atoms or of perfluoroalkylcarboxylic acids, tetramethylene sulphone (or sulpholane), and aliphatic nitriles such as acetonitrile.

Acetic acid is generally preferred, in particular when the substrate to be oxidized is cyclohexane.

The catalyst preferably contains cobalt, manganese, a mixture of cobalt with one or more other metals such as manganese, chromium, iron, zirconium, hafnium or copper, or a mixture of manganese with one or more other metals such as chromium, iron, zirconium, hafnium or copper. Among the cobalt-based mixtures, catalysts comprising either cobalt and chromium, cobalt, chromium and zirconium, cobalt and iron, cobalt and manganese or cobalt and zirconium and/or hafnium are more particularly suitable. This catalyst is used for the oxidation of cyclohexane in the form of compounds of these metals which are soluble in the reaction medium.

The reaction mixture to be treated by the process of the invention contains, as a guide, on a weight for weight basis, from 1% to 99% of unconverted hydrocarbon, from 1% to 40% of carboxylic acids formed, from 0.1% to 10% of water, from 0.001% to 5% of the metal(s) contained in the catalyst, and from 0.1% to 10% of other oxidation reaction products, the remainder consisting of the solvent.

The step of distillation of the lower phase, or where appropriate of the reaction mixture, is carried out such that most, and as far as is possible all, of the unconverted cyclohexane which may still be present in this lower phase is separated from the adipic acid. The reaction intermediates, such as cyclohexanol, cyclohexanone, cyclohexyl acetate and lactones (esentially butyrolactone and valerolactone) are also separated out, as is the solvent, preferably comprising a carboxylic acid.

The distillation step is generally carried out at a temperature from 25° C. to 250° C. and at an absolute pressure of between 10 Pa and atmospheric pressure. Preferably, the temperature of the mixture during the distillation will be maintained between 70° C. and 150° C.

The distillation can, if necessary, be carried out in several successive steps, in particular in the preferred mode in which it is desired to remove the majority, for example more than 90% and even more than 99%, of the aliphatic carboxylic acid solvent.

One advantageous variant of the process of the invention consists in introducing steam into the reaction mixture before or during the distillation step.

This operation can allow better entrainment of certain compounds present in the mixture subjected to the distillation. It can also achieve a partial or complete hydrolysis of the carboxylic esters which may also be found in the mixture to be distilled.

The distillate obtained in the distillation operation described above comprises the various volatile compounds and water. These volatile compounds are valorizable and thus recycled in a new cyclohexane oxidation reaction, after an at least partial removal of the water, by any known means, in particular by azeotropic distillation.

In accordance with the invention, an organic solvent or a mixture comprising at least one organic solvent in accordance with the invention is added to the distillation residue to dissolve the adipic acid formed and optionally to precipitate the catalysts. The amount of solvent added represents from 0.1 to 20 times the weight of the mixture obtained after the said distillation. Preferably, the amount of solvent added represents from 0.5 to 10 times this weight.

This operation thus consists in dissolving the adipic acid in the minimum amount of hot solvent, which optionally allows the catalyst to be separated out by hot filtration of the solution. The crystallization itself is performed according to the usual techniques, by gradual cooling of the organic solution. Generally, the solution is seeded using crystals of adipic acid.

The adipic acid obtained by this crystallization can then be recrystallized from water, in order to achieve the purity required for the main applications in which it is used.

Variants can be performed without departing from the context of the present invention. Thus, certain operations can be carried out before the step of crystallization of the adipic acid from an organic solvent. It is advantageous, for example, to perform an additional oxidation of the intermediate oxidation compounds present in the polar liquid phase, after most, and preferably all, of the unconverted cyclohexane has been separated out and before the other compounds and the carboxylic acid solvent have been separated out. This additional oxidation can be performed with molecular oxygen or a gas containing it, the oxidation being catalysed by the initial catalyst still present in the said polar phase, or alternatively using an oxygen donor such as hydrogen peroxide or an organic hydroperoxide.

Such an additional oxidation is then followed by the total or partial separation of the carboxylic acid solvent, before the step of crystallization of the adipic acid in an organic solvent.

After this optional additional oxidation operation, the adipic acid is crystallized as indicated above.

The process of the invention can also be completed by a reaction to reduce the reducible impurities which may be present in the technical-grade adipic acid obtained by crystallization from an organic solvent.

Such a reduction is advantageously a hydrogenation with hydrogen, after redissolving the technical-grade adipic acid in a solvent such as water, if necessary in the presence of a hydrogenation catalyst not dissolved in the medium. The hydrogenation catalyst is separated from the medium at the end of the reaction.

Finally, the recrystallization from water can also be preceded by an oxidative finishing operation using nitric acid or alternatively by a known treatment of adsorption and decolourization, for example using carbon black.

The process of the invention makes it possible to obtain, in particular, after the recrystallization from water, adipic acid which can satisfy the specifications set for its use in the synthesis of polyamide 6-6 or polyurethanes.

Other details and advantages of the invention will emerge more clearly in the light of the examples given below, purely as a guide and for the purposes of illustration.

EXAMPLE 1

Preparation of Oxidation Masses

A jacketed titanium 1.5 l autoclave equipped with a six-blade turbomixer and various openings for the introduction of the reagents and fluids or for the removal of the reaction products and fluids, and which has been purged beforehand with nitrogen, is loaded at room temperature with the following:

| | |
|---|---|
| Cobalt acetate tetrahydrate | 4.0 g (16 mmol) |
| Acetic acid | 357 g |
| Cyclohexane | 292.5 g |
| Cyclohexanone | 3.2 g (32.7 mmol) |

After closing the autoclave, the nitrogen pressure is brought to 20 bar, the stirring (1000 rpm) is started and the temperature is brought to 105° C. over 20 minutes. The nitrogen is then replaced with 20 bar of depleted air (5% oxygen). The flow rate of inlet gas is adjusted to 250 liters per hour.

After an induction of about ten minutes, during which there is no consumption of oxygen, the temperature rises by 2 to 3° C. and the oxygen begins to be consumed. The inlet oxygen titre is gradually raised to 21%. The oxygen titre at the reactor outlet remains less than 5% throughout the test. The temperature in the autoclave ranges between 104.9 and 105.1° C.

When 50 liters of oxygen have been consumed (degree of conversion of about 20%), continuous injection of the liquid phase is commenced: injection of an acetic acid solution containing 1.1% by weight of cobalt acetate tetrahydrate and 1.45% by weight of cyclohexanone at a flow rate of 4.6 ml/min (stabilized regime) and injection of cyclohexane at a flow rate of 5 ml/min (stabilized regime). The liquid product is stored continuously in a 7 litre decanter at 70° C.

After 380 min from the start of the reaction, the air is gradually replaced with nitrogen and the contents of the autoclave are transferred into the decanter. The decanter contains a two-phase mixture. The upper, essentially cyclohexane phase, which contains only a small amount of products and cobalt, is separated out. The acetic lower phase (2675 g) contains most of the oxidation products and the cobalt.

The acetic phase is subjected to a first distillation under the following conditions:
pressure: 60 kPa
temperature: 135° C.

The distillation residue 1 is subjected to a further, more rigorous distillation intended to remove the volatile organic compounds it contains by means of an injection of steam at 150° C. under a pressure of 10 kPa. The results obtained are collated in the table below:

| Compound | Initial untreated ma | Distillation residu | Distillation residu |
|---|---|---|---|
| Cyclohexanone | 285 mmol | 90 mmol | negligible |
| Cyclohexyl acetate | 19.0 mmol | 37.0 mmol | negligible |
| Free cyclohexanol | 245 mmol | 58 mmol | negligible |
| Glutaric acid* | 249 mmol | 249 mmol | 249 mmol |
| Succinic acid* | 164.9 mmol | 164.9 mmol | 164.9 mmol |
| Adipic acid* | 2115 mmol | 2115 mmol | 2115 mmol |
| Hydroxycaproic acid | 50.0 mmol | 50.0 mmol | 50.0 mmol |
| 3-Hydroxyadipic acid | 104 mmol | 104 mmol | 104 mmol |
| Butyrolactone | 85.3 mmol | 58.0 mmol | negligible |
| Valerolactone | 34.0 mmol | 12.2 mmol | negligible |
| Total mass | 2675 g | 595 g | 452 g |

*Total acid (free and esterified)

EXAMPLE 2
Crystallization from Water

A portion of the distillation residue 2 (112 g) is subjected to a crystallization from water (250 g). The mixture is heated to 70° C. and is then gradually cooled to room temperature.

After filtration and washing with water, 60 g of crude adipic acid are obtained.

A recrystallization from water of this crude adipic acid gives a purified adipic acid (A) containing:
succinic acid: 0.0003%
glutaric acid: <0.0001%
cobalt: <0.0002%

The cobalt catalyst is in the crystallization water and the washing water.

EXAMPLE 3
Crystallization from Acetone

Another portion of the distillation residue 2 of Example 1 (225 g) is diluted in 700 ml of acetone and brought to reflux. The organic materials are dissolved. The undissolved cobalt salts are filtered off while hot and recovered for recycling.

The filtrate is gradually cooled to room temperature (about 20° C.).

After filtration and washing with acetone, 120 g of crude (or technical-grade) adipic acid are obtained.

A recrystallization from water of this crude adipic acid gives a purified adipic acid (B) containing:
succinic acid: 0.0002%
glutaric acid: <0.0001%
cobalt: <0.0002%

The adipic acid batches (A) and (B) are subjected to a heating test. This test consists in heating 50 g of each batch to 215° C. for 205 min and then placing each of them in 415 ml of aqueous 5% ammonia solution. The absorbence at 454 nm of the ammonium adipate solutions obtained is then measured.

The results below are obtained, expressed as relative absorbences, the reference adipic acid (A) representing the value 1:
adipic acid (A): 1
adipic acid (B): 0.25

The purified adipic acid (B) according to the present invention contains fewer impurities liable to become coloured on heating.

EXAMPLE 4
Crystallization from 1,4-dioxane

A portion of the distillation residue 1 (112 g) of Example 1 is subjected to a crystallization from 1,4-dioxane (250 g). The mixture is heated to 70° C., filtered while hot and then gradually cooled to room temperature.

After filtration and washing with water, 50 g of crude adipic acid are obtained.

A recrystallization from water of this crude adipic acid gives a purified adipic acid (C) containing:
succinic acid: 0.0002%
glutaric acid: <0.0001%
cobalt: <0.0002%

The cobalt catalyst was recovered by hot filtration of the dioxane solution.

EXAMPLE 5
Crystallization from Acetonitrile

A portion of the distillation residue 1 (112 g) of Example 1 is subjected to a crystallization from acetonitrile (450 g). The mixture is heated to 80° C., filtered while hot and then gradually cooled to room temperature.

After filtration and washing with water, 65 g of crude adipic acid are obtained.

A recrystallization from water of this crude adipic acid gives a purified adipic acid (D) containing:
succinic acid: 0.0005%
glutaric acid: <0.0001%
cobalt: <0.0002%

The cobalt catalyst was recovered by hot filtration of the acetonitrile solution.

EXAMPLE 6
Crystallization from Isopropanol

A portion of the distillation residue 1 (112 g) of Example 1 is subjected to a crystallization from isopropanol (250 g). The mixture is heated to 100° C., filtered while hot and then gradually cooled to room temperature.

A portion of the distillation residue 1 (112 g) of Example 1 is subjected to a crystallization from butyl acetate (250 g). The mixture is heated to 100° C., filtered while hot and then gradually cooled to room temperature.

After filtration and washing with water, 58 g of crude adipic acid are obtained.

A recrystallization from water of this crude adipic acid gives a purified adipic acid (E) containing:
succinic acid: 0.0002%
glutaric acid : <0.0001%
cobalt: <0.0002%

The adipic acid batches (A) and (C) to (E) are subjected to a heating test.

This test consists in heating 50 g of each batch to 215° C. for 205 min and then placing each of them in 415 ml of aqueous 5% ammonia solution.

The absorbance at 454 nm of the ammonium adipate solutions obtained is then measured.

The following results are obtained, expressed as relative absorbances, the reference adipic acid (A) representing the value 1:

| Purified adipic acids | Relative absorbance at 454 nM |
|---|---|
| A (Ex. 3) | 1 |
| C (Ex. 4) | 0.3 |
| D (Ex. 5) | 0.2 |
| E (Ex. 6) | 0.5 |

The adipic acids (B), (C) and (D) purified according to the present invention contain fewer impurities liable to become coloured on heating than the adipic acid (A), thus demonstrating the effects of the crystallization from an organic solvent.

In another embodiment of the process of the invention, the crystallization from an organic solvent in accordance with the invention can be carried out on adipic acid crystallized from water. This crystallization from an organic solvent can be completed again by purification treatments as described above and/or by another crystallization from water.

The examples given above can be applied to a reaction medium obtained from the hydroxycarbonylation of butadiene.

What is claimed is:

1. A process for treating the reaction mixture obtained from the direct oxidation of hydrocarbons into carboxylic acids, in the liquid phase, in a solvent and in the presence of a catalyst dissolved in the reaction medium, said process comprising:

separating when the composition of the reaction mixture allows it, the phases by settling into two liquid phases: a nonpolar upper phase, comprising the unconverted hydrocarbon, and polar lower phase comprising the solvent, the acids formed, the catalyst and some of the other reaction products and the unconverted hydrocarbon;

distilling the polar lower phase or, where appropriate, all of the reaction mixture, thus separating, on the one hand, a distillate comprising at least some of the most volatile compounds, the solvent, the reaction intermediates and substantially all of the water, and, on the other hand, the distillation residue comprising the carboxylic acids formed and the catalyst;

adding to the distillation residue an organic solvent in which the carboxylic acid has a solubility of less than or equal to 15% by weight at 20° C. or a mixture comprising at least one of said organic solvent, said organic solvent being selected from the group consisting of ethers, alcohols, esters, nitriles, amides, sulphoxides, carbonates, and halogen, nitro or phosphorous-containing compounds;

optionally filtering the medium obtained; and recovering said carboxylic acids by crystallization of the acids formed by cooling and/or evaporation of the said organic solvent.

2. The process according to claim 1, wherein the solubility of the carboxylic acid in the solvent at a temperature of 100° C., or at its boiling point if this is lower than 100° C., is at least 5% higher than that at 20° C. in the same solvent.

3. The process according to claim 1, wherein the hydrocarbon used as starting material is selected from these group consisting of alkanes, cycloalkanes and alkylaromatic hydrocarbons having from 3 to 20 carbon atoms.

4. The process according to claim 3, wherein the hydrocarbon used as starting material comprises cycloalkanes which contain a ring having from 5 to 12 carbon atoms.

5. The process according to claim 4, wherein the hydrocarbon used as the starting material is cyclohexane.

6. The process according to claim 5, wherein the carboxylic acid formed is adipic acid.

7. The process according to claim 1, wherein the crystallization solvents are selected from the group consisting of 1,4-dioxane; diglyme (diethylene glycol dimethyl ether); tetrahydrofuran; aliphatic, cycloaliphatic, aromatic or arylaliphatic ketones such as acetone, methyl isobutyl ketone, methyl ethyl ketone, methyl isopropyl ketone, methyl phenyl ketone, cyclohexanone, n-butanol; isopropanol; 3-methoxyethanol; acetonitrile; dimethylformamide; acetamide; dichloromethane; ethyl acetate; 1,2-dichloroethane; dimethyl sulphoxide; nitromethane; and N-methylpyrrolidone.

8. The process according to claim 1, wherein the solvent used in the step of oxidation of the hydrocarbon is at least a partial solvent for adipic acid and is selected from the group consisting of polar protic solvents and polar aprotic solvents.

9. The process according to claim 8, wherein the solvent used in the oxidation step comprises aliphatic acids having from 1 to 9 carbon atoms.

10. The process according to claim 1, wherein the catalyst comprises cobalt, manganese, a mixture of cobalt with one or more other metals chosen from manganese, chromium, iron, zirconium, hafnium and copper or a mixture of manganese with one or more other metals selected from the group consisting of chromium, iron, zirconium, hafnium and copper.

11. The process according to claim 10, wherein the catalyst comprising cobalt-based mixtures comprising either cobalt and chromium, or cobalt, chromium and zirconium, or cobalt and iron, or cobalt and manganese or cobalt and zirconium and/or hafnium.

12. The process according to claim 1, wherein the step of distillation of the polar lower phase, or where appropriate of the reaction mixture, is carried out at a temperature from 25° C. to 250° C., and under an absolute pressure of between 10 Pa and atmospheric pressure.

13. The process according to claim 1, wherein the carboxylic acid obtained after crystallization from the organic solvent is recrystallized from water.

14. Process according to claim 13, characterized in that the hydrocarbon used as starting material is cyclohexane.

15. Process according to one of claims 8 to 14, characterized in that the solvent used in the oxidation of the hydrocarbon is an at least partial solvent for adipic acid and is chosen from polar protic solvents and polar aprotic solvents.

16. Process according to one claims 8 to 15, characterized in that the solvent is chosen from aliphatic acids containing from 1 to 9 carbon atoms and is preferably acetic acid.

17. Process according to one of claims 8 to 16, characterized in that the catalyst contains cobalt, manganese, a mixture of cobalt with one or more other metals chosen from manganese, chromium, iron, zirconium, hafnium and copper or a mixture of manganese with one or more other metals chosen from chromium, iron, zirconium, hafnium and copper.

18. Process according to claim 17, characterized in that the catalyst is chosen from cobalt-based mixtures comprising either cobalt and chromium, cobalt, chromium and zirconium, cobalt and iron, cobalt and manganese or cobalt and zirconium and/or hafnium.

19. Process according to one of claims 8 to 18, characterized in that the step of distillation of the polar lower phase, or where appropriate of the reaction mixture, is carried out at a temperature from 25° C. to 250° C., preferably from 70° C. to 150° C., and under an absolute pressure of between 10 Pa and atmospheric pressure.

20. Process according to one of claims 8 to 19, characterized in that the adipic acid obtained after crystallization from the organic solvent is recrystallized from water.

* * * * *